United States Patent [19]

Rösner et al.

[11] 4,198,407
[45] Apr. 15, 1980

[54] SUBSTITUTED 2-PHENYL-1,2,4-TRIAZINE-3,5(2H,4H)-DIONES, AND COCCIDIOSTATIC AGENTS CONTAINING SAME

[75] Inventors: Manfred Rösner, Eppstein; Wolfgang Raether, Dreieich, both of Fed. Rep. of Germany

[73] Assignee: Hoechst Aktiengesellschaft, Frankfurt am Main, Fed. Rep. of Germany

[21] Appl. No.: 906,638

[22] Filed: May 16, 1978

[30] Foreign Application Priority Data

May 18, 1977 [DE] Fed. Rep. of Germany ....... 2722537

[51] Int. Cl.$^2$ .................. C07D 253/06; A61K 31/53
[52] U.S. Cl. ................. 424/249; 260/239.7; 544/182
[58] Field of Search ........... 544/182; 424/249; 260/239.7

[56] References Cited

U.S. PATENT DOCUMENTS

| 3,883,527 | 5/1975 | Brennan | 544/182 |
| 3,883,528 | 5/1975 | Mylari | 544/182 |
| 3,896,124 | 7/1975 | Mylari | 544/182 |
| 3,912,723 | 10/1975 | Miller | 544/182 |

FOREIGN PATENT DOCUMENTS

| 2231378 | 5/1974 | France | 544/182 |
| 2234298 | 6/1974 | France | 544/182 |

*Primary Examiner*—Natalie Trousof
*Assistant Examiner*—Jane T. Fan
*Attorney, Agent, or Firm*—Curtis, Morris & Safford

[57] ABSTRACT

Novel substituted 2-phenyl-1,2,4-triazine-3,5-(2H,4H)-diones are described as well as a process for their manufacture. The novel compounds may be used as chemotherapeutics, especially as coccidiostatic agents.

10 Claims, No Drawings

SUBSTITUTED 2-PHENYL-1,2,4-TRIAZINE-3,5(2H,4H)-DIONES, AND COCCIDIOSTATIC AGENTS CONTAINING SAME

2-Aryl-1,2,4-triazine-3,5-(2H,4H)-diones having coccidiostatic properties and the preparation thereof are known from German published Patent Application nos. 2149645, 2358851 and 2423972.

Subject of the present invention are new substituted 2-phenyl-1,2,4-triazine-3,5-(2H,4H)-diones of general formula I,

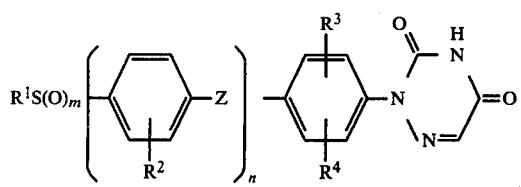
(I)

wherein $R^1$ and $R^2$ independently from each other represent hydrogen, a linear or branched alkyl radical having 1 to 4 carbon atoms, $R^3$ and $R^4$ independently from each other represent hydrogen or halogen, Z represents oxygen, sulfur, the sulfoxide group >S=O, or the group

m represents the numbers 0, 1 or 2, and n represents 0 or 1, as well as the salts of these compounds with physiologically acceptable bases especially the alkali metal salts, the alkali earth metal salts or the ammonium salts thereof.

Preference is given to those compouns of formula I, wherein $R^1$ represents methyl, $R^2$ represents hydrogen or methyl, $R^3$ and $R^4$ represent hydrogen or chlorine, especially preferred in 3- and 5-position, Z represents oxygen or sulfur, m represents the number 0 and n represents the number 1. Special efficiency has been exhibited, among these substances, by 2-[3,5-dichloro-4-(4-methylthiophenoxy)-phenyl]-1,2,4-triazine-3,5-(2H,4H)-dione.

Subject of the invention is also a process for preparing compounds of formula I, which comprises either (a) decarboxylating a compound having general formula II

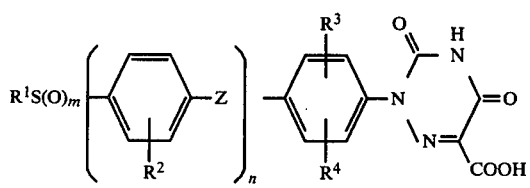
(II)

or (b) treating a compound having general formula III

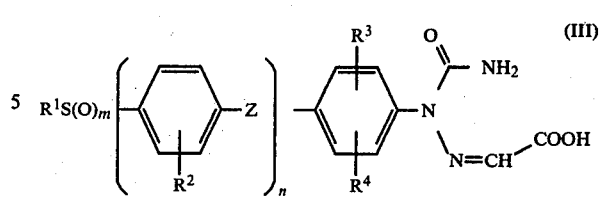
(III)

with a dehydrating agent, or (c) reacting a compound of general formula IV

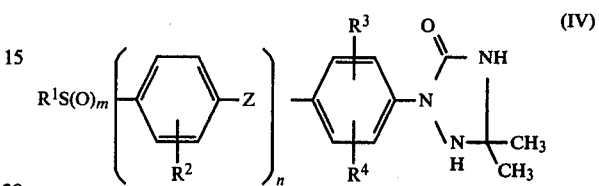
(IV)

with glyoxylic acid, the substituents and indices in the general formulae II, III and IV having the same meaning as in formula I.

(a) Decarboxylation of the compounds of formula II is suitably carried out by heating to 100°–300° C., preferably to 120°–280° C. Either the dry compound of formula (II) may be heated, or with preference a liquid being inert under the reaction conditions and having a high boiling point may be added, such as ethylene glycol, toluene, xylene, quinoline or a mixture of biphenyl and diphenyloxide. The reaction may be accelerated by an auxiliary agent acting as catalyst for the decarboxylation, e.g. pulverized copper, thiourea compounds or mercapto carboxylic acids having suitably from 2 to 8 carbon atoms, preferably mercapto acetic acid. The molar ratio may be kept between 0.1 to 1 and 10 to 1 of mercapto carboxylic acid to 6-carboxy-1,2,4-triazinedione of formula II. The time needed for decarboxylation depends on the specific reaction conditions, especially the temperature, and keeps within a wide range of from 10 minutes to 30 hours.

(b) Dehydration is suitably carried out by heating a compound of formula III to a temperature of from 50° to 150° C., preferably from 100° to 130° C., during for 2 to 8 hours, with the addition of at least an equivalent amount of a basic substance such as sodium hydroxide, triethylamine, pyridine, methylpyridine or sodium acetate, or of an acid substance such as acetic acid anhydride, polyphosphoric acid.

(c) The saponification, condensation and cyclization reactions are suitably carried out in the same reaction vessel without isolating the intermediates. Thus, a compound of formula IV is heated with glyoxylic acid, optionally in the presence of an at least equivalent amount of an acid auxiliary agent such as sodium acetate/acetanhydride, sulfuric acid or polyphosphoric acid, at a temperature of from 50° to 180° C., preferably from 100° to 150° C.

If in a triazine dione of formula I, thus obtained Z represents sulfur or sulfoxide and/or m represents 0 or 1 such a compound may be converted into the corresponding sulfoxide, with a stoichiometric amount of an oxidizing agent such as hydrogen peroxide or a peracid, peracetic or m-chloroperbenzoic acid, suitably at room temperature, or such a compound may be converted into the corresponding sulfonyl compounds by using an excess of such an oxidizing agent, at a reaction temperature of from 50° to 150° C., preferably from 100° to 120° C.

The compounds of formula I may be converted by adding, suitably a molar equivalent, of alkali metal or alkali earth metal hydroxide or ammonia to yield the corresponding salts, sodium hydroxide, sodium hydride, potassium hydroxide, calcium hydroxide, calcium hydride or ammonia being preferred.

The compounds of general formula II are prepared by reacting a compound of general formula V

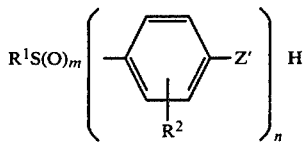

with a compound of general formula VI,

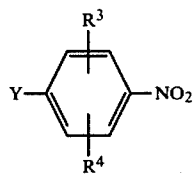

wherein Y represents halogen, preferably fluorine or chlorine, to yield a compound of general formula VII

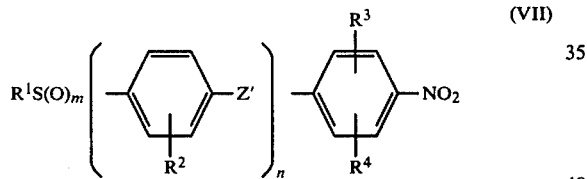

wherein the substituents $R^1$ to $R^4$ and the indices m and n in the formulae V to VII have the meanings as given for formula I, while Z' represents oxygen or sulfur.

The corresponding sulfoxide compounds or sulfonyl compounds are prepared by oxidation of a corresponding sulfur compound of general formula VII with hydrogen peroxide or of a peracid such as peracetic acid or m-chloroperbenzoic acid. Corresponding oxidations may also be carried out with the compounds of formulae VIII, XI, XII or II.

The nitro compounds of general formula VII are subjected to a reduction reaction, e.g. with Raney-nickel or with iron according to Bechamp, in order to yield an amino compound of general formula VIII

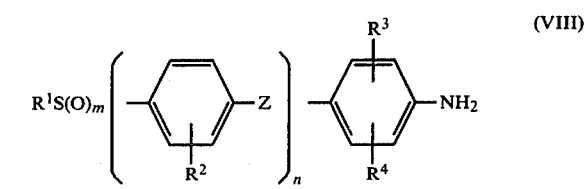

This compound is reacted with a nitrite in the presence of an acid HX to yield an aromatic diazonium salt of general formula IX,

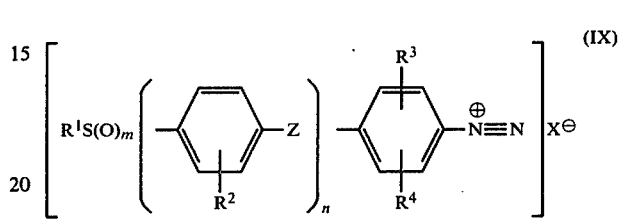

wherein in formula VIII and in formula IX $R^1$ to $R^4$, Z, m and n have the meanings given for formula I, while $X^{(-)}$ represents an acid anion, preferably chloride, bromide, sulfate, tetrafluoroborate or tetrachlorozincate.

Instead of the free anilines of general formula VIII, there may as well be used in the reaction their salts with an acid HX, the acid anion $X^{(-)}$ having preferably the mentioned meaning.

The diazonium salts of general formula IX are subsequently reacted with a compound of formula X,

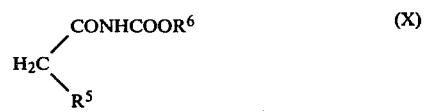

wherein $R^5$ represents —CN or —CONHCOOR$^6$ and $R^6$ represents alkyl having 1 to 4 carbon atoms, preferably methyl or ethyl to yield the corresponding substituted phenylhydrazone of the general formula XI,

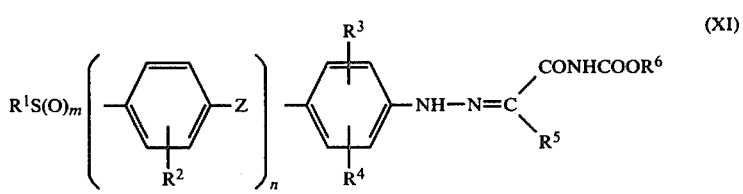

wherein $R^1$ to $R^4$, Z, m, n, $R^5$ and $R^6$ have the aforementioned meanings, which in turn is reacted with the use of a basic catalyst such as sodium acetate in a protic solvent such as glacial acetic acid, at boiling temperature to yield a 1,2,4-triazine-3,5-(2H,4H)-dione of general formula XII,

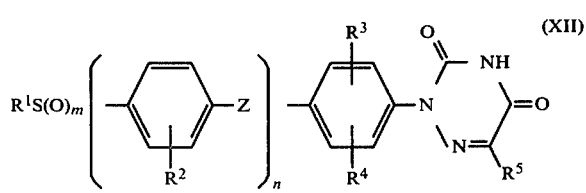

wherein $R^1$ to $R^4$, Z, m, n, $R^5$ and $R^6$ have the afore given meanings. The dione of formula XII is then saponified in an acid medium by adding a strong acid such as sulfuric acid, at elevated temperature, to yield a 6-carboxy compound of general formula II.

The compounds of general formula III are prepared by reacting a substituted hydrazine of general formula XIII,

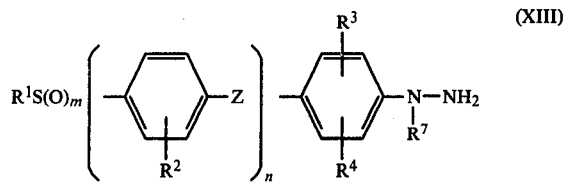

wherein $R^7$ represents hydrogen and $R^1$ to $R^4$, Z, m and n have the meanings given for formula I, with bromocyanogen (XIII, $R^7$=CN), by saponifying subsequently with an alkali

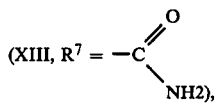

and by reacting the resulting compound with glyoxylic acid, in the presence of an acid such as hydrochloric acid to yield a compound of formula III.

The compounds of formula IV are prepared by reacting a substituted hydrazine of general formula XIII ($R^7$=hydrogen) in an acid solution first with acetone and then with potassium cyanate.

The preparation of the nitro compounds of general formula VII, is suitably carried out in a dipolar aprotic solvent, such as dimethylformamide, with the addition of a basic compound such as an acetate, carbonate or hydroxide of an alkali metal or alkali earth metal, or of a tertiary amine such as pyridine or triethylamine.

The reaction time varies from 5 minutes to 5 hours, depending on the conditions applied.

The reaction temperature varies from 20° to 200° C., and is preferably the boiling temperature of the solvent employed.

The reduction of the nitro compounds of formula VII to yield an aniline of formula VIII may be carried out according to anyone of the numerous known processes (cf. Houben-Weyl, Methoden der organischen Chemie, vol. 11/1, pg. 360 sq.). Preference is given to catalytic hydrogenation, for example with Raney nickel or with iron according to Bechamp.

The diazonium salts IX are prepared in known manner (cf. Houben-Weyl, Methoden der organischen Chemie, Band 10/3, pg. 1 sq.), by diazotizing the anilines VIII.

The reaction of a diazonium salt of formula IX with a compound of formula X is carried out in a solvent or in a mixture of solvents, advantageously in a protic solvent, preferably in water or glacial acetic acid, or mixtures thereof, at a temperature of from 0° to 30° C., preferably from 10° to 20° C., at a pH of from 4 to 12, preferably from 4 to 8. Operating in the presence of basic compounds such as acetates, carbonates, hydroxides of the alkali metals or alkali earth metals or of tertiary amines such as pyridine or triethylamine, is advantageous.

The reaction time, depending on the condition applied, varies from 1 hour to 22 hours. The compounds of formula XI are isolated in usual manner by filtering off the precipitated reaction product, optionally after the addition of water.

The phenyl hydrazone of formula XI is cyclized in a solvent or a mixture of solvents, preferably in a protic solvent, especially in glacial acectic acid or water or mixtures thereof, advantageously in the presence of a basic compound such as an acetate, carbonate, or hydroxide of an alkali metal or alkali earth metal or of a tertiary amine such as pyridine or triethylamine. The cyclization is carried out at elevated temperature, preferably from 80° to 160° C., and especially advantageously at the boiling temperature of the solvent mixture employed. The reaction time varies from 1 hour to 5 hours, preferably from 2 to 4 hours. The dione of formula XII is isolated in usual manner, after dilution with water, by filtering off.

The saponification of the compounds of formula XII is carried out advantageously in an aqueous mineral acid, such as hydrochloric acid, sulfuric acid or phosphoric acid, or in a mixture of sulfuric acid, acetic acid and water. The saponification may be carried out also in an alkaline medium with a hydroxide of an alkali metal or an alkali earth metal. The hydrolysis is carried out at elevated temperature, preferably from 80° to 160° C., and especially advantageously at the boiling temperature of the mixture employed. The reaction time varies from 1 to 3 hours.

The compounds of formula II may be prepared in a less complicated manner by not isolating the intermediate product of formula XII, optionally not isolating the intermediate product of formula XI.

The compounds of formula I according to the invention are new chemotherapeutics, especially coccidiostatic agents. They are further intermediate products for the synthesis of medicaments.

Even a small quantity of a compound of formula I exhibits a remarkable efficiency against various protozoa causing coccidiosis in poultry and in other animal species, while showing a good compatibility. Moreover, compounds act upon coccidiosis viruses that are resistant against several drugs.

In principle, the compounds of formula I may be administered as such, suitably incorporated in drinking water or food. They are preferably applied in mixtures with a suitable carrier material. Suitable carrier materials may be the common fodder mixtures. In that case, an active substance of formula I is added to the fodder at a concentration rate of 0.5–300 ppm., preferably from 1–50 ppm.

A coccidiostatic composition according to the invention may contain, for example, 6 g of the afore mentioned substance in admixture to 994 g of calcium carbonate. 500 g of this mixture are incorporated in a common fodder mixture to yield a total of 1.000 kg of coccidiostatic fodder.

The following Examples illustrate the invention

EXAMPLE 1

1-(4-methyl-thio-phenoxy)-4-nitrobenzene of formula VII 28.2 g (0.2 mol) of 1-fluoro-4-nitrobenzene and 28 g (0.2 mol) of 4-(methylthio)-phenol are stirred with 27.6 g (0.2 mol) of potassium carbonate in 100 ml of dimethylformamide, under reflux, for one hour and a half.

After cooling there are added 300 ml of water, while stirring. The liquid is filtered with suction from the precipitate which in turn is washed till neutral and recrystallized from isopropanol, melting point 58°–59° C.

In this reaction the 1 fluoro-4-nitrobenzene may be replaced by an equimolar quantity of 1-chloro-4-nitrobenzene.

4-(4-methylthio-phenoxy)-aniline of formula VIII 52.5 g (0.2 mol) of 1-(4-methylthio)-phenoxy-4-nitrobenzene in 600 ml of methanol are hydrogenated with a catalytic quantity of Raney nickel, at room temperature. After termination of absorbing hydrogen, the catalyst is filtered off with suction and the solution concentrated in vacuo.

The remaining oil is dissolved in 2 N-hydrochloric acid while still hot. The hydrochloride of 4-(4-methylthiophenoxy)-aniline precipitates upon cooling. After being recrystallized from water, the melting point is 183°–184° C.

4-(4-methylthio-phenoxy)-phenyldiazonium chloride of formula IX

A solution of 2.8 g (0.04 mol) of sodium nitrite in 15 ml of water is added dropwise, at an internal temperature of max. 10° C., to 10.7 g (0.04 mol) of 4-(4-methylthiophenoxy)-aniline in 100 ml of glacial acetic acid and 7.5 ml of conc. hydrochloric acid. Then stirring is continued for 15 minutes.

The diazonium salt solution thus obtained is further reacted, without isolating the salt, to yield 4-(4-methylthio-phenoxy-phenylhydrazonomalonyl diurethane of formula XI A mixture of 8 g sodium acetate and 10 g (0.04 mol) of malonyl diurethane is added to the diazonium salt solution prepared sub (c), and agitation is continued. The slowly forming yellow precititate is stirred with water after three hours, filtered off which suction and washed till neutral, m.pt. 195°–197° C.

2-[4-(4-methylthio-phenoxy)-phenyl)]-6-carboxy-1,2,4-triazine-3,5-(2H,4H)-dione of formula II 14.6 (0.03 mol) of 4-(4-(methylthio)-phenoxy)-phenylhydrazonomalonyl diurethane are stirred in 150 ml of glacial acetic acid with 2.5 g of sodium acetate for two hours, at reflux temperature. The solution is allowed to cool slightly, 15 ml of sulfuric acid (50% strength) are added and the solution is heated further under reflux for two hours, followed by stirring with water, filtering off with suction, washing till neutral, meltg. pt. 190°–193° C. decompos.

2-[4-(4-methylthio-phenoxy)-phenyl)]-1,2,4-triazine-3,5-(2H,4H)-dione of formula I 3.3 g (0.01 mol) of 2-[(4-4-methylthio-phenoxy)-phenyl)]-6-carboxy-1,2,4-triazine-3,5-(2H,4H)-dione and 3 g of thiourea are heated under reflux for 5 hours in 20 ml of diethylene glycol dimethyl ether. The result is then completed to 100 ml with the addition of water, stirred, filtered off with suction and washed with water. The residue is recrystallized from isopropanol with the addition of activated charcoal, meltg. pt. 210°–211° C.

2-[4-(4-methylsulfinylphenoxy)-phenyl]-1,2,4-triazine-3,5-(2H,4H)-dione of formula I 0.615 g of 2-[4-(4-methylthio-phenoxy)-phenyl]-1,2,4-triazine-3,5-(2H,4H)-dione are dissolved, while still hot, in 20 ml of glacial acetic acid. 0.2 ml of hydrogen peroxide (35% strength) are added at 60° C., the solution is allowed to cool further and is stirred at room temperature for one more hour.

After adding 30 ml of water, the solution is filtered off with suction, washed with water, meltg. pt. 229°–230° C.

2-[4-(4-methylsulfonylphenoxy)-phenyl]-1,2,4-triazine-3,5-(2H,4H)-dione of formula I 0.7 g of 2-(4-(4-methylsulfinylphenoxy)-phenyl)-1,2,4-triazine-3,5-(2H,4H)-dione are blended in 15 ml glacial acetic acid with 2.2 ml of hydrogen peroxide (35% strength) and stirred at 100°–110° C. for 30 minutes.

The result is stirred with 15 ml of water, filtered off with suction and subsequently washed with water, meltg. pt. 188°–190° C.

The following compounds are prepared by analogy with the process of Example 1

EXAMPLE 2

From 1-chloro-4-nitrobenzene and 4-methylthio-thiophenol: 1-(4-methylthio-phenylthio)-4-nitrobenzene, meltg. pt. 70°–70.5° C.
From 1-(4-methylthio-phenylthio)-4-nitrobenzene, by reducing with iron according to Bechamp:
4-(4-methylthio-phenylthio)-aniline, meltg. pt. 96°–97° C., resulting in
4-(4-methylthio-phenylthio)-phenyldiazonium salt, by diazotizing.
The reaction of 4-(4-methylthio-phenylthio)-phenyldiazonium salt with malonyl diurethane yields:
4-(4-methylthio-phenylthio)-phenylhydrazonomalonyl diurethane, meltg. pt. 185°–186° C.
2-[4-(4-methylthio-phenylthio)-phenyl]-6-carboxy-1,2,4-triazine-3,5-(2H,4H)-dione, meltg. pt. 198°–200° C. decompos. results from
4-(4-methylthio-phenylthio)-phenylhydrazonomalonyl-diurethane by cyclization and saponification.
2-[4-(4-methylthio-phenylthio)-phenyl]-1,2,4-triazine-3,5-(2H,4H)-dione, meltg. pt. 174°–175° C. results from
2-[4-(4-methylthio-phenylthio)-phenyl]-6-carboxy-1,2,4-triazine-3,5-(2H,4H)-dione, by decarboxylation with thioglycolic acid.

EXAMPLE 3

1-(3-methyl-4-methylthio-phenoxy)-4-nitrobenzene, meltg. pt. 64°–65° C.
results from 1-chloro-4-nitrobenzene and 3-methyl-4-methylthio-phenol
4-(3-methyl-4-methylthio-phenoxy)-aniline, as hydrochloride, meltg. pt. 216°–222° C., results from
1-(3-methyl-4-methylthio-phenoxy)-4-nitrobenzene by catalytic hydrogenation.
By diazotizing is obtained
4-(3-methyl-4-methylthio-phenoxy)-phenyldiazonium salt.
The reaction of this diazonium salt with malonyl diurethane provides:
4-(3-methyl-4-methylthio-phenoxy)-phenylhydrazonomalonyl diurethane, meltg. pt. 190°–192° C.
By cyclization and saponification is obtained from 4-(3-methyl-4-methylthio-phenoxy)-phenylhydrazonomalonyl diurethane:

2-[4-(3-methyl-4-methylthio-phenoxy)-phenyl]-6-carboxy-1,2,4-triazine-3,5-(2H,4H)-dione, meltg. pt. 206°–207° C. decompos.

By decarboxylation with thioglycolic acid is obtained from 2-[4-(3-methyl-4-methylthio-phenoxy)-phenyl]-6-carboxy-1,2,4-triazine-3,5-(2H,4H)-dione:

2-[4-(3-methyl-4-methylthio-phenoxy)-phenyl]-1,2,4-triazine-3,5-(2H,4H)-dione, meltg. pt. 145°–148° C.

EXAMPLE 4

1,3-dichloro-2-(4-methylthio-phenoxy)-5-nitrobenzene, meltg. pt. 94°–95° C. is obtained from 1,2,4-trichloro-5-nitrobenzene and 4-methylthiophenol.

3,5-dichloro-4-(4-methylthio-phenoxy)-aniline, meltg. pt. 119°–120° C., is obtained by catalytic hydrogenation from 1,3-dichloro-2-(4-methylthio-phenoxy)-5-nitrobenzene.

Diazotizing this result yields 3,5-dichloro-4-(4-methylthio-phenoxy)-phenyl-diazonium salt.

The reaction of this diazonium salt with malonyl diurethane provides:

3,5-dichloro-4-(4-methylthio-phenoxy)-phenylhydrazono-malonyl diurethane, meltg. pt. 168°–169° C.

2-[3,5-dichloro-4-(4-methylthio-phenoxy)-phenyl]-6-[(N-ethoxycarbonyl)-carbamoyl]-1,2,4-triazine-3,5-(2H,4H)-dione, meltg. pt. 201°–202° C., is obtained from 3,5-dichloro-4-(4-methylthio-phenoxy)-phenyl-hydrazonomalonyl diurethane, by cyclization.

The result is saponified with sulfuric acid (50% strength) to yield:

2-[3,5-dichloro-4-(4-methylthio-phenoxy)-phenyl]-6-carboxy-1,2,4-triazine-3,5-(2H,4H)-dione, meltg. pt. 212°–213° C. decompos.

2-[3,5-dichloro-4-(4-methylthio-phenoxy)-phenyl]-1,2,4-triazine-3,5-(2H,4H)-dione, meltg. pt. 160°–162° C. is obtained from 2-[3,5-dichloro-4-(4-methylthio-phenoxy)-phenyl]-6-carboxy-1,2,4-triazine-3,5-(2H,4H)-dione, by decarboxylizing with thioglycolic acid in xylene.

2-[3,5-dichloro-4-(4-methylsulfinyl-phenoxy)-phenyl]-1,2,4-triazine-3,5-(2H,4H)-dione, meltg. pt. 208°–210° C. is obtained from 2-[3,5-dichloro-4-(4-methylthio-phenoxy)-phenyl]-1,2,4-triazine-3,5-(2H,4H)-dione, with a stoichiometric quantity of hydrogen peroxide.

2-[3,5-dichloro-4-(4-methylsulfinyl-phenoxy)-phenyl]-1,2,4-triazine-3,5-(2H,4H)-dione, meltg. pt. 256° C. is obtained from 2-[3,5-dichloro-4-(4-methylthio-phenoxy)-phenyl]-1,2,4-triazine-3,5-(2H,4H)-dione, with an excess of hydrogen peroxide.

EXAMPLE 5

1,2,3-trichloro-5-nitrobenzene and 4-methylthio-thiophenol provide:

1,3-dichloro-2-(4-methylthio-phenylthio)-5-nitrobenzene, melting point 135°–139° C.

1,3-dichloro-2-(4-methylthio-phenylthio)-5-nitrobenzene, by reduction with iron according to Bechamp, yields:

3,5-dichloro-4-(4-methylthio-phenylthio)-aniline, meltg. pt. 104°–105° C.

The result, subjected to diazotizing, yields 3,5-dichloro-4-(4-methylthio-phenylthio)-phenyl-diazonium salt.

The reaction of this diazonium salt with malonyl diurethane yields:

3,5-dichloro-4-(4-methylthio-phenylthio)-phenylhydrazonomalonyl diurethane, meltg. pt. 133°–136° C.

3,5-dichloro-4-(4-methylthio-phenylthio), by cyclization and saponification, yields:

2-[3,5-dichloro-4-(4-methylthio-phenylthio)-phenyl]-6-carboxy-1,2,4-triazine-3,5-(2H,4H)-dione, meltg. pt. 167°–169° C. decomp.

2-[3,5-dichloro-4-(4-methylthio-phenylthio)-phenyl]-6-carboxy-1,2,4-triazine-3,5-(2H,4H)-dione, by decarboxylizing with thioglycolic acid yields:

2-[3,5-dichloro-4-(4-methylthio-phenylthio)-phenyl]-1,2,4-triazine-3,5-(2H,4H)-dione, meltg. pt. 141°–142° C.

2-[3,5-dichloro-4-(4-methylthio-phenylthio)-phenyl]-1,2,4-triazine-3,5-(2H,4H)-dione, with a stoichiometric quantity of hydrogen peroxide, yields:

2-[3,5-dichloro-4-(4-methylsulfinyl-phenylsulfinyl)-phenyl]-1,2,4-triazine-3,5-(2H,4H)-dione, meltg. pt. 195°–197° C.

2-[3,5-dichloro-4-(4-methylthio-phenylthio)-phenyl]-1,2,4-triazine-3,5-(2H,4H)-dione, with an excess of hydrogen peroxide, yields:

2-[3,5-dichloro-4-(4-methylsulfonyl-phenylsulfonyl)-phenyl]-1,2,4-triazine-3,5-(2H,4H)-dione, meltg. pt. 263° C.

EXAMPLE 6

1,2,3-trichloro-5-nitrobenzene and 3-methyl-4-methylthiophenol yield:

1,3-dichloro-2-(3-methyl-4-methylthio-phenoxy)-5-nitro-benzene, melting point 83°–84° C.

1,3-dichloro-2-(3-methyl-4-methylthio-phenoxy)-5-nitro-benzene, by reduction with iron according to Bechamp, yields:

3,5-dichloro-4-(3-methyl-4-methylthio-phenoxy)-aniline, m.p. 137°–138° C.

This aniline yields, by diazotizing:

3,5-dichloro-4-(3-methyl-4-methylthio-phenoxy)-phenyl-diazoniumchloride.

3,5-dichloro-4-(3-methyl-4-methylthio-phenoxy)-phenyl-diazoniumchloride and malonyldiurethane yield:

3,5-dichloro-4-(3-methyl-4-methylthio-phenoxy)-phenyl-hydrazono malonyldiurethane, m.p. 183° C. decomp.

3,5-dichloro-4-(3-methyl-4-methylthio-phenoxy)-phenyl-hydrazono malonyldiurethane, by cyclization and saponification, yields:

2-[3,5-dichloro-4-(3-methyl-4-methylthio-phenoxy)-phenyl]-6-carboxy-1,2,4-triazine-3,5-(2H,4H)-dione, m.p. 222° C., decomp.

2-[3,5-dichloro-4-(3-methyl-4-methylthio-phenoxy)-phenyl]-6-carboxy-1,2,4-triazine-3,5-(2H,4H)-dione, by decarboxylation with thioglycolic acid, yields:

2-[3,5-dichloro-4-(3-methyl-4-methylthio-phenoxy)-phenyl]-1,2,4-triazine-3,5-(2H,4H)-dione, m.p. 69°–71° C.

EXAMPLE 7

4-methylthio-phenyldiazonium chloride is obtained from 4-methylthio-aniline-hydrochloride, by diazotizing.

4-methylthio-phenyldiazoniumchloride yields, by reaction with malonyldiurethane:

4-methylthio-phenylhydrazonomalonyldiurethane, m.p. 189° C.

4-methylthio-phenylhydrazonomalonyldiurethane, by cyclization and saponification, yields:

2-(4-methylthio-phenyl)-6-carboxy-1,2,4-triazine-3,5-(2H,4H)-dione, m.p. 221° C. decomp.

2-(4-methylthio-phenyl)-6-carboxy-1,2,4-triazine-3,5-(2H,4H)-dione, by decarboxylizing with thiourea in diethylene glycol dimethylether, yields:

2-(4-methylthio-phenyl)-1,2,4-triazine-3,5-(2H,4H)-dione, m.p. 245°–246° C.

EXAMPLE 8

1,2,3-trichloro-5-nitrobenzene and methylmercaptane yield:

1,3-dichloro-2-methylthio-5-nitrobenzene, m.p. 66°–68° C.

1,3-dichloro-1-methylthio-5-nitrobenzene, by reduction with iron according to Bechamp, yields:

3,5-dichloro-4-methylthio-aniline, m.p. 122°–126° C. Diazotizing this result yields:

3,5-dichloro-4-methylthio-phenyldiazonium salt.

3,5-dichloro-4-methylthio-phenyldiazonium salt yields, by reaction with malonyl diurethane:

3,5-dichloro-4-methylthio-phenylhydrazonomalonyl diurethane, m.p. 177°–178° C.

3,5-dichloro-4-methylthio-phenylhydrazonomalonyl diurethane, by cyclization and saponification, yields:

2-(3,5-dichloro-4-methylthio-phenyl)-6-carboxy-1,2,4-triazine-3,5-(2H,4H)-dione, m.p. 240° C. decomp.

2-(3,5-dichloro-4-methylthio-phenyl)-6-carboxy-1,2,4-triazine-3,5-(2H,4H)-dione, by decarboxylation with thioglycolic acid, yields:

2-(3,5-dichloro-4-methylthio-phenyl)-1,2,4-triazine-3,5-(2H,4H)-dione, m.p. 179°–180° C.

What is claimed is:

1. A substituted 2-phenyl-1,2,4-triazine-3,5-(2H,4H)-dione of the formula:

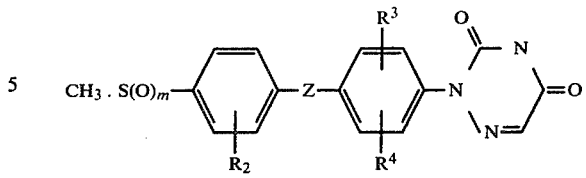

wherein:
$R^2$ is hydrogen or methyl,
$R^3$ and $R^4$ are chlorine,
Z is oxygen, sulfur, or SO, and
m is 0 or 1,
as well as the salts of these compounds with physiologically acceptable bases.

2. A compound according to claim 1 wherein said salt is selected from alkali metal, alkaline earth metal and ammonium salts.

3. A compound according to claim 1 wherein $R^3$ and $R^4$ represent chlorine in the 3- and 5-positions.

4. A compound according to claim 1 which is 2[3,5-dichloro-4-(4-methylthio-phenoxy)-phenyl]-1,2,4-triazine-3,5-(2H,4H)-dione.

5. A compound according to claim 1 which is 2-[3,5-dichloro-4-(4-methylsulfinyl-phenoxy)-phenyl]-1,2,4-triazine-3,5-(2H,4H)-dione.

6. A compound according to claim 1 which is 2-[3,5-dichloro-4-(4-methythio-phenylthio)-phenyl]-1,2,4-triazine-3,5-(2H,4H)-dione.

7. A compound according to claim 1 which is 2-[3,5-dichloro-4-(4-methylsulfinyl-phenylsulfinyl)-phenyl]-1,2,4-triazine-3,5-(2H,4H)-dione.

8. A compound according to claim 1 which is 2-[3,5-dichloro-4-(3-methyl-4-methylthio-phenoxy)-phenyl]-1,2,4-triazine-3,5-(2H,4H)-dione.

9. A composition useful in the treatment of coccidiosis comprising a pharmaceutically acceptable carrier and an effective amount of a compound as defined in claim 1.

10. A method of treating protozoal diseases by administering to a patient an effective amount of a compound as claimed in claim 1.

* * * * *